United States Patent [19]

Giordano et al.

[11] Patent Number: 4,861,903
[45] Date of Patent: Aug. 29, 1989

[54] INTERMEDIATES FOR PREPARING OPTICALLY ACTIVE CARBOXYLIC ACIDS

[75] Inventors: Claudio Giordano, Vicenza; Graziano Castaldi, Briona, both of Italy

[73] Assignee: Zambon spa, Vicenza, Italy

[21] Appl. No.: 891,349

[22] Filed: Jul. 31, 1986

[30] Foreign Application Priority Data

Jul. 31, 1985 [IT] Italy ................................ 21802 A/85

[51] Int. Cl.[4] ................. C07D 317/12; C07D 317/44; C07D 317/18; C07D 317/26
[52] U.S. Cl. ................................... 549/434; 549/455; 549/454; 549/453; 549/452; 549/450; 549/448; 549/436; 549/429
[58] Field of Search ............... 549/453, 448, 450, 452, 549/454, 455, 434, 436, 429

[56] References Cited

U.S. PATENT DOCUMENTS 4,560,777 12/1985 Giordano et al. ................ 549/374
4,605,758 8/1986 Schloemer ........................ 562/459

FOREIGN PATENT DOCUMENTS 1186319 4/1985 Canada .
0035305 9/1981 European Pat. Off. .
0034871 10/1981 European Pat. Off. .
0048136 3/1982 European Pat. Off. .
0081993 6/1983 European Pat. Off. .
0101124 2/1984 European Pat. Off. .

OTHER PUBLICATIONS

Ulrich et al., C.A., 115,561j, (1967).
Journal of Organic Chemistry, vol. 43, No. 25, Dec. 8, 1978, pp. 4689, 4876–4878.
Journal of the Chemical Society, Perkin Transactions I, Organic and Bio-Organic Chemistry, 1982, pp. 2575–2580.
Angewandte Chemie, vol. 23, 1984, pp. 413–419.
Asymmetric Synthesis, vol. 4, 1984, The Chrial Carbon Pool and Chiral Sulfur, Nitrogen, Phosphorus, and Silicon Centers, pp. 10–57.

Primary Examiner—Nicky Chan
Attorney, Agent, or Firm—Cushman, Darby & Cushman

[57] ABSTRACT

A process is described for preparing optically active alpha-arylalkanoic acids consisting of rearranging an optically active ketal of formula

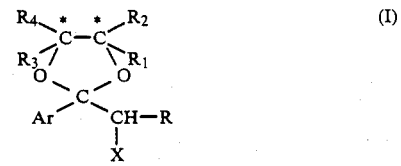

in which the substituents have the meaning given in the description of the invention.

2 Claims, No Drawings

INTERMEDIATES FOR PREPARING OPTICALLY ACTIVE CARBOXYLIC ACIDS

This invention relates to a process for preparing optically active alpha-arylalkanoic acids and more particularly a process for preparing said acids by rearranging optically active ketals.

Numerous alpha-arylalkanoic acids are known for their pharmaceutical properties (anti-inflammatory, analgesic).

These include 2-(4-isobutylphenyl)-propionic acid known as Ibuprofen, 2-(3-phenoxyphenyl)-propionic acid known as Fenoprofen, 2-(2-fluoro-4-diphenylyl)-propionic acid known as Flurbiprofen, 2-[4-(2-thienyl-carbonyl)-phenyl]-propionic acid known as Suprofen, 2-(6-methoxy-2-naphthyl)-propionic acid the (S) isomer of which is known as Naproxen, and others.

A further group of alpha-arylalkanoic acids are useful as intermediates in the preparation of pyrethrum insecticides. These include 2-(4-chlorophenyl)-3-methyl-butyric acid and 2-(4-difluoromethoxyphenyl)-3-methyl-butyric acid.

Various processes are known for preparing alpha-arylalkanoic acids by rearranging ketals of the appropriate alpha-functionalised alkyl-aryl-ketones, for example the processes described in European patent application Nos. 34871 and 35305 (Blaschim), 48136 (Sagami) and 101124 (Zambon) and in J. Chem. Soc., Perkin I, 11, 2575 (1982) and Angew. Chem. Int. Ed., 23, 413 (1984).

It is also known to prepare optically active alpha-functionalised alkyl-aryl-ketones and from these to prepare the corresponding ketals and rearrange them by known methods (European patent application No. 81993, Syntex).

We have now discovered the subject of the present invention, namely a process for directly preparing optically active alpha-functionalised ketals which by rearrangement form optically active alpha-arylalkanoic acids.

The process according to the invention consists of halogenating a ketal of formula

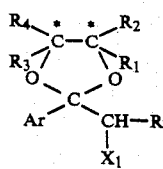
(I-A)

in which
Ar represents an aryl, possibly substituted;
R represents a $C_1$–$C_4$ alkyl;
$X_1$ represents a hydrogen atom;
$R_1$, $R_2$, $R_3$ and $R_4$ independently represent a hydrogen atom, a $C_1$–$C_{10}$ alkyl possibly substituted with from 1 to 4 substituents chosen from halogen atoms, $C_1$–$C_4$ alkoxy, hydroxyl, formyl, alkylenedioxy or benzyloxy groups; a phenyl possibly substituted with from 1 to 3 halogen atoms, $C_1$–$C_4$ alkyl or $C_1$–$C_4$ alkoxy; or one only of $R_1$, $R_2$, $R_3$ and $R_4$ represents a carboxyl or one of its functional derivatives such as an alkylester including of an optically active alcohol, an amide or an alkaline salt; or $R_1$ and $R_3$ or $R_2$ and $R_4$ together constitute a tri or tetramethylene chain possibly alkyl-substituted;

on condition that the substituents $R_1$, $R_2$, $R_3$ and $R_4$ are such that at least one of the carbon atoms indicated by an asterisk is a centre of asymmetry, and if both the carbon atoms indicated by as asterisk are asymmetric the compound I-A is optically active.

Halogenation of the compound I-A leads to the compound

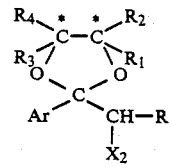
(I-B)

in which Ar, R, $R_1$, $R_2$, $R_3$ and $R_4$ have the meanings given for the formula I-A and $X_2$ represents a chlorine, bromine or iodine atom.

If desired, it is possible to prepare from the compounds I-B the compounds of formula

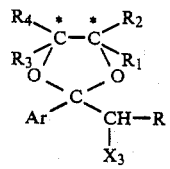
(I-C)

in which Ar, R, $R_1$, $R_2$, $R_3$ and $R_4$ have the meanings given for formula I-A, and $X_3$ represents a hydroxyl, acyloxy, alkylsulphonyloxy or arylsulphonyloxy group.

The compounds of formula I-A, I-B and I-C are new.

A subject of the present invention is therefore compounds of formula

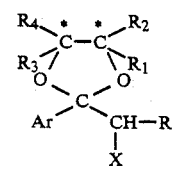
(I)

in which Ar, R, $R_1$, $R_2$, $R_3$ and $R_4$ have the meanings given for formulas I-A, I-B and I-C, and X represents a hydrogen atom, a chlorine, bromine or iodine atom, or a hydroxyl, acyloxy, alkylsulphonyloxy or arylsulphonyloxy group; the substituents $R_1$, $R_2$, $R_3$ and $R_4$ being such that at least one of the carbon atoms indicated by an asterisk is a centre of asymmetry, the compound of formula I being optically active even when X is a hydrogen atom.

The halogenation reaction of the compounds I-A proceeds surprisingly in a stereoselective manner to provide compounds of formula I-B in which one of the two diastereoisomers with respect to the centre of asymmetry constituted by the carbon atom carrying the substituent $X_2$ prevails.

In this manner the compound I-B is obtained stereoselectively in which that isomer prevails which has the carbon atom carrying the substituent $X_2$ in the R or S configuration, depending on the configuration of the carbon atoms indicated by an asterisk.

Depending on the conditions under which the compound I-B is transformed into the compound I-C, this latter will either maintain or invert the configuration at the carbon atoms carrying the substituents $X_3$ with respect to that of the same centre of asymmetry in the compound I-B.

Rearranging the compounds I-B or the compounds I-C (in which $X_3$ is other than a hydroxyl) by known methods leads to the corresponding optically active alpha-arylalkanoic acids of formula

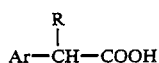

(II)

(in which Ar and R have the meanings given for the formula I-A) or their immediate precursors such as esters, in which one of the two enantiomers prevails.

The required optically active form is a function of the configuration of the carbon atom carrying the substituent $X_2$ or $X_3$ in the compounds I-B and I-C respectively, and in particular when this centre of asymmetry has mainly S configuration, the corresponding alpha-arylalkanoic acid will have mainly S configuration.

The compounds of formula I-A are prepared by reacting the appropriate aryl-alkyl-ketone of formula

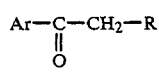

(III)

(in which Ar and R have the meanings given for the formula I-A) with an optically active diol of formula

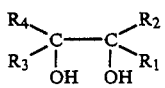

(IV)

(in which $R_1$, $R_2$, $R_3$ and $R_4$ have the meanings given for formula I-A).

The reaction between compound II and compound IV is carried out in the presence of a dehydrating agent such as a trialkylorthoformate, or by azeotropically distilling the water formed during the reaction.

Alternatively, the compounds of formula I-A can be prepared by trans-ketalisation, ie by reacting the ketone III with a ketal of the diol IV.

Examples of ketals of the diol IV which are useful for preparing the compounds of formula I by trans-ketalisation include 2,2-dimethyl-1,3-dioxolane derivatives obtained by ketalisation of the diol IV with acetone.

Compounds of formula III include:
1-(4-isobutyl-phenyl)-propan-1-one,
1-(3-phenoxy-phenyl)-propan-1-one,
1-(2-fluoro-4-diphenylyl)-propan-1-one,
1-[4-(2-thienylcarbonyl)-phenyl]-propan-1-one,
1-(6-methoxy-2-naphthyl)-propan-1-one,
1-(5-bromo-6-methoxy-2-naphthyl)-propan-1-one,
1-(6-hydroxy-2-naphthyl)-propan-1-one,
1-(4-chlorophenyl)-3-methyl-butan-1-one,
1-(4-difluoromethoxy-phenyl)-3-methyl-butan-1-one.

Compounds of formula IV include:
possibly substituted aliphatic diols such as
(2R)-1,2-propanediol,
(2S)-1,2-propanediol,
(2R,3R)-2,3-butanediol,
(2S,3S)-2,3-butanediol,
(1R)-1-phenyl-1,2-ethanediol,
(1S)-1-phenyl-1,2-ethanediol,
(1R,2R)-1,2-diphenyl-1,2-ethanediol,
(1S,2S)-1,2-diphenyl-1,2-ethanediol,
(2R)-2-methyl-1,2-butanediol,
(2S)-2-methyl-1,2-buanediol,
(2R,3R)-2,3-pentanediol,
(2S,3S)-2,3-pentanediol,
(2R,3R)-1-chloro-2,3-butanediol,
(2S,3S)-1-chloro-2,3-butanediol,
(3R,4R)-3,4-dimethyl-3,4-hexanediol,
(3S,4S)-3,4-dimethyl-3,4-hexanediol,
(3R,4R)-3,4-hexanediol,
(3S,4S)-3,4-hexanediol,
(R)-3-benzyloxy-1,2-propanediol,
(S)-3-benzyloxy-1,2-propanediol,
(1R,2R)-cyclohexanediol,
3-methyl-(1R,2R)-cyclohexanediol;
carbolic acids and derivatives such as
(2R)-2,3-dihydroxy-propionic acid,
(2S)-2,3-dihydroxy-propionic acid,
methyl(2R)-2,3-dihydroxy-propionate,
methyl(2S)-2,3-dihydroxy-propionate,
ethyl(2R)-2,3-dihydroxy-propionate,
ethyl(2R)-2,3-dihydroxy-propionate,
(2R)-2,3-dihydroxy-propionamide,
(2S)-2,3-dihydroxy-propionamide,
N,N-dimethyl-(2R)-2,3-dihydroxy-propionamide,
N,N-dimethyl-(2S)-2,3-dihydroxy-propionamide,
(2R,3R)-2,3-dihydroxy-butanoic acid,
(2S,3S)-2,3-dihydroxy-butanoic acid,
ethyl(2R,3R)-2,3-dihydroxy-butanoate,
ethyl(2S,3S)-2,3-dihydroxy-butanoate;
sugars and derivatives, possibly partly protected as acetanides, such as
D(−)-arabinose,
L(+)-arabinose,
D(+)-arabitol,
L(−)-arabitol,
5-deoxy-L-arabinose,
D(−)-ribose,
L(+)-ribose,
2-deoxy-ribose,
D(+)-xylose,
L(−)-xylose,
D-mannitol,
1,2,5,6-di-O-isopropylene-D-mannitol,
L(−)-mannose,
D(+)-mannose;
and also the various compounds containing a diol structure reported in "Asymmetric Synthesis", vol. 4, pag. 10–57, J. D. Morrison and J. W. Scott, Academic Press Inc. (1984).

The compounds of formula III are known compounds which can be easily prepared by a Friedel-Crafts reaction between the appropriate aromatic compound and the chosen acyl chloride (for example propionyl chloride).

The compounds of formula IV are also known compounds and are either commercially available or easily prepared at least as a mixture of stereoisomers, which can often be separated by chromatographic methods. Some of the compounds of formula IV are available in the form of ketals (for example acetonides) from which, as stated heretofore, it is likewise possible to prepare the compounds I-A.

It is important to note that in compounds of formula I-A there are two or three centres of asymmetry (not considering other centres of asymmetry in the substituents Ar and R) which in the formula given hereinafter are indicated by the letters a, b and c.

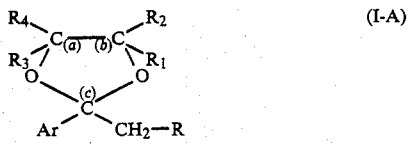

(I-A)

Three centres of asymmetry (a, b and c) are present when $R_1$ is different from $R_2$, $R_3$ is different from $R_4$ and the pair of substituents $R_1$ and $R_2$ is different from the pair $R_3$ and $R_4$.

In contrast, only the centres of asymmetry a (or b) and c are present when $R_3$ is different from $R_4$ but $R_1$ is equal to $R_2$ (or vice versa).

The halogenation of the compounds I-A, which according to the experimental conditions given hereinafter proceeds in a diastereoselective manner, leads to compounds I-B in which a new centre of asymmetry (d) is created constituted by the carbon atom carrying the substituent $X_2$

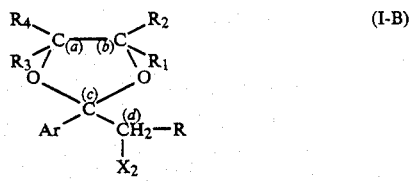

(I-B)

We have found that the configuration of the asymmetric centres a and b determines the configuration of the new centre of asymmetry d, even when only two of them are present.

We have also found that the configuration of the centre of asymmetry d, independently of that of the other centres of asymmetry, determines the enantiometic ratio of the alpha-arylalkanoic acids obtained from the compounds of formula I-B (or I-C) by the procedures described hereinafter.

The halogenation is carried out by treating the compound I-A with a halogenating agent in an inert solvent at a temperature of between ambient and −70° C.

The halogenating agents which can be used in said reaction include bromine ($Br_2$), quaternary ammonium perhalides, iodine chloride, sulphuryl cloride, cupric chloride or bromide, N-chloro or N-bromo succinimide, N-chloro-phthalimide, pyridine perbromide, phosphorus trichloride, hexachlorocyclohexanedienone, etc.

Suitable inert solvents include chlorinated hydrocarbons such as carbon tetrachloride, methylene chloride, 1,1-dichloroethane, 1,2-dichloroethane; aromatic hydrocarbons such as benzene, toluene, chlorobenzene; cyclic ethers such as tetrahydrofuran, and also acetonitrile, hexane and in general aprotic solvents of low polarity.

The reaction involving the halogenation of the compounds of formula I-A has very surprisingly been found to be diastereoselective, this term meaning that in the compounds I-B obtained in this manner there prevails one of the two pairs of diastereoisomers (R or S) with respect to the centre of asymmetry d.

By suitably choosing the stereoisomerism of the compound of formula I-A and thus suitably choosing the stereoisomerism of the diol IV it is possible to obtain the compound of formula I-B in which the pair of diastereoisomers R or S prevails, at choice, with respect to the centre of asymmetry d.

By way of example, bromination of 2-ethyl-2-aryl-(4R,5R)-4,5-dimethyl-1,3-dioxolane (I-A in which $R_1=R_3=CH_3$, $R_2=R_4=H$) leads to the corresponding 2-(1-bromoethyl)-2-aryl-(4R,5R)-4,5-dimethyl-1,3-dioxolane (I-B in which $X_2=Br$, $R_1=R_3=CH_3$, $R_2=R_4=H$) in which the carbon atom carrying the substituent $X_2$ (=Br) has mainly R configuration.

Likewise, bromination of 2-ethyl-2-aryl-(4S,5S)-4,5-dimethyl-1,3-dioxolane leads to the corresponding 2-(1-bromoethyl)-2-aryl-(4S,5S)-4,5-dimethyl-1,3-dioxolane in which the carbon atom carrying the substituent $X_2$ (=Br) has mainly S configuration.

The compounds of formula I-C can be prepared by direct tosylation of compounds I-A by reacting these with hydroxy-tosyloxy-iodobenzene [J. Org. Chem., 47, 2487, (1982)]. Again in this case the reaction is diastereoselective.

From the compounds of formula I-C in which $X_3$=p.toluenesulphonyl, compounds I-C in which $X_3$=OH are obtained by hydrolysis, and from these the other compounds of formula I-C are obtained by acylation with the appropriate acyl halide.

The compounds of formula I-B and I-C (in which $X_3$ is other than hydroxyl) can be rearranged by applying known methods for rearranging alpha-functionalised ketals into alpha-arylalkanoic acids, for example by simply heating in a protic polar solvent or in an aprotic dipolar solvent in the presence of a substance of high dielectric constant, in a neutral or slightly alkaline environment. Depending on the reaction solvent, the product will be either an alkaline salt or an ester of the corresponding acid of formula II. This latter is easily obtained in free form by acidification or by hydrolysis of the immediate precursor ester respectively.

The compounds of formula I-B can be directly transformed into the corresponding alpha-arylalkanoic acids or their precursors by reacting the compound of formula I in an inert solvent with a metal catalyst pertaining to the soft or borderline group of Lewis acids (J. March, "Advanced Organic Chemistry", page 229, 3rd Edition, John Wiley and Son). Specific examples of these compounds include organic or inorganic salts of the following cations:

$Cu^+$, $Ag^+$, $Cu^{++}$, $Pd^{++}$, $Pt^{++}$, $Hg^{++}$, $Fe^{++}$, $Co^{++}$, $Zn^{++}$, $Sn^{++}$, $Sb^{+++}$, and $Bi^{+++}$.

The reaction provides compounds of formula II in the form of esters.

As stated heretofore, the configuration of the centre of asymmetry d in compounds I-B and I-C determines the configuration of the alpha-arylalkanoic acid prepared from them.

More particularly, starting for example from compounds of formula I-B in which the carbon atom carrying the halogen ($X_2$) has mainly S configuration, the corresponding alpha-arylalkanoic acids in which the enantiomer of S configuration or vice versa prevails are obtained by rearrangement.

This aspect is particularly important considering that an alpha-arylalkanoic acid of special pharmaceutical interest is 2-(6-methoxy-2-naphthyl)-propionic acid, which is marketed in optically active form as the S(+) enantiomer, under the name of Naproxen.

One aspect of the present invention is therefore a process for preparing S(+)-2-(6-methoxy-2-naphthyl)-propionic acid (Naproxen) in pure form or in a mixture of enantiomers in which the S(+) enantiomer prevails.

Said process, which is carried out as heretofore described, uses as its starting substance and as intermediates the ketals of formula

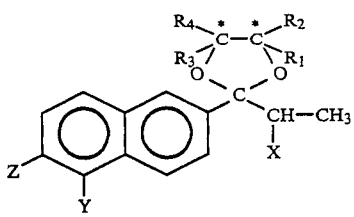

(I-b)

in which X, $R_1$, $R_2$, $R_3$ and $R_4$ have the meanings given for formula I, Y represents a hydrogen or bromine atom, and Z represents a methoxy, hydroxyl or $O^-M^+$ group where $M^+$ is the cation of an alkaline metal.

The process proceeds in a manner analogous to that heretofore described starting with the ketal (I-B) in which X=H, by way of the corresponding halogenated ketal I-b (X=Cl, Br, I) (or acetoxylated, methylated, tosylated etc.), then rearranging this latter.

If the compound I-b is brominated with bromine, the corresponding derivative in which X=Br is obtained. This latter on rearrangement and hydrolysis provides 2-(5-bromo-6-methoxy-2-naphthyl)-propionic acid, which is an immediate precursor of Naproxen. In this respect, the bromine atom in position 5 is easily eliminated by hydrogenolysis in accordance with conventional methods (for example by treatment with hydrazine in the presence of palladium on carbon).

The following examples are given hereinafter to better illustrate the invention.

EXAMPLE 1

Preparation of 4(R),5(R)-dimethyl-2-ethyl-2-(6-methoxy-2-naphthyl)-1,3-dioxolane (1)

A mixture of 1-(6-methoxy-2-naphthyl)-propan-2-one (4.07 g; 19 mmoles), 2(R),3(R)-butanediol (1.80 g; 20 mmoles), trimethylorthoformate (2.12 g; 20 mmoles) and methanesulphonic acid (0.01 g; 1 mmole) is heated to 55° C. for 3 hours, the volatile substances being distilled off in a stream of nitrogen.

The reaction mixture is then poured into an aqueous 8% sodium bicarbonate solution and extracted with dichloromethane. The pooled organic extracts are then washed with water and dried with sodium sulphate. Evaporating the solvent leaves a residue which after chromatography through a silica gel column (eluent hexane:ether=9:1) provides a pure compound (1) in the form of an oil (5.16 g; 18 mmoles; yield 95%).

I.R. $^1$H-NMR and mass spectrometry are consistent with the assigned structure.

$[\alpha]_D^{20} = +33.8°$ (C=1%, CHCl$_3$)

EXAMPLE 2

Preparation of 4(R),5(R)-dimethyl-2-(1-bromoethyl)-2-(5-bromo-6-methoxy-2-naphthyl)-1,3-dioxolane (2)

A solution of Br$_2$ (1.49 g; 9.32 mmoles) in dichloromethane (2 ml) precooled to −30° C. is added over 10 minutes to a solution of the compound (1) prepared in accordance with Example 1 (1.30 g; 4.54 mmoles) in dichloromethane (12 ml), maintained at −30° C. under nitrogen.

After 2.5 hours at −30° C., a solution of triethylamine (1.4 ml; 20 mmoles) in dichloromethane (2 ml) maintained at −30° C. is added.

The mixture is then raised to ambient temperature, washed with water, dried with sodium sulphate and the solvent evaporated under vacuum. In this manner the compound (2) is obtained with quantitative yield (2.00 g; 4.50 mmoles).

The diastereoisomeric ratio determined by $^1$H-NMR shows RRR:RRS=66:34.

I.R., $^1$H-NMR and mass spectrometry are consistent with the assigned structure.

EXAMPLE 3

Preparation of the 3-hydroxy-2-butylester of 2-(5-bromo-6-methoxy-2-naphthyl)-propionic acid (3)

A solution of silver tetrafluoroborate (430 mg; 2.18 mmoles) in 1,2-dichloroethane (4 ml) is added dropwise to a mixture of the compound (2), prepared in accordance with Example 2 in a diastereoisomeric ratio RRR:RRS=62.5:37.5 (0.8 g; 1.8 mmoles), 1,2-dichloroethane (8 ml) and water (60 mg; 3.33 mmoles) maintained at 15° C. under agitation.

After 4 hours the reaction mixture is poured into water (10 ml) and filtered through celite, the filtrate being washed with methylene chloride (5 ml). The organic phases are washed with water and dried with sodium sulphate.

Evaporating the solvents leaves a residue which after column chromatography provides the two diastereoisomers of the 3-hydroxy-2-butylester of 2-(5-bromo-6-methoxy-2-naphthyl)-propionic acid in which the asymmetric carbon atom of the acid part has 52% of R configuration and 38% of S configuration (determined by $^1$H-NMR analysis).

I.R., $^1$H-NMR and mass spectrometry are consistent with the assigned structure.

EXAMPLE 4

Preparation of 2-ethyl-2-(6-methoxy-2-naphthyl)-4(R)-methoxycarbonyl-1,3-dioxolane (4)

A mixture of 1-(6-methoxy-2-naphthyl)-propan-1-one (1.07 g; 5 mmoles), 2,2-dimethyl-4(R)-methoxycarbonyl-1,3-dioxolane (0.96 g; 6 mmoles), carbon tetrachloride (1 ml) and methanesulphonic acid (2 mg; 0.02 mmoles) is heated under reflux for 2 hours. 1 mg of methanesulphonic acid is added, and the mixture heated for a further 1 hour.

The reaction mixture is then cooled, poured into an aqueous 8% sodium carbonate solution and extracted with dichloromethane.

The pooled organic extracts are washed with water and dried with sodium sulphate. Evaporating the solvent leaves an impure product which is chromatographed through silica gel (eluent hexane:ethyl ether=75:25) to obtain the pure compound (4) (0.66 g; 2.1 mmoles; yield 42%) in the form of two diastereoisomers.

I.R., $^1$H-NMR and mass spectrometry are consistent with the assigned structure.

EXAMPLE 5

Preparation of
2-(1-bromoethyl)-2-(5-bromo-6-methoxy-2-naphthyl)-4(R)-methoxycarbonyl-1,3-dioxolane (5)

A solution of bromine (505 mg; 3.16 mmoles) in carbon tetrachloride (1 ml) is added to a solution of the two diastereoisomers of compound (4), prepared as described in Example 4 (500 mg; 1.58 mmoles) in carbon tetrachloride, kept under agitation at 15° C.

After complete decoloration of the bromine, the reaction mixture is added dropwise to an aqueous 10% sodium carbonate solution and extracted with methylene chloride.

The pooled organic phases are washed with water and dried with sodium sulphate.

Evaporating the solvent leaves the required product (5) in the form of diastereoisomers, with quantitative yield.

I.R., $^1$H-NMR and mass spectrometry are consistent with the assigned structure.

EXAMPLE 6

Preparation of
2-(5-bromo-6-methoxy-2-naphthyl)-propionic acid (6)

A solution of silver tetrafluoroborate (370 mg; 1.94 mmoles) in 1,2-dichloroethane (2 ml) is added dropwise to a solution of the diastereoisomers of compound (5) prepared as described in Example 5 (750 ml; 1.58 mmoles) in 1,2-dichloroethane (4 ml) and water (72 mg; 4 mmoles) kept under agitation at 15° C.

After 5 hours the reaction mixture is poured into water (40 ml) and filtered through celite, the filtrate being washed with methylene chloride (10 ml).

The organic phase is washed with water (2×20 ml) and dried with sodium sulphate.

Evaporating the solvent under reduced pressure leaves a residue (655 mg) which is dissolved in dioxane (5 ml) and concentrated hydrochloric acid (5 ml). The solution is heated to 70° C. for 6 hours.

The reaction mixture is cooled and extracted with ethyl ether.

The pooled organic phases are then extracted with 10% sodium carbonate. The aqueous solution is acidified to pH 1 with hydrochloric acid and extracted with ether.

The organic extracts are dried with sodium sulphate and the solvent evaporated to obtain the pure acid (6) (361 mg; 1.17 mmoles). Yield 74% calculated with respect to the compound (5) used.

$[\alpha]_D^{20} = -8.15°$

EXAMPLE 7

Operating as described in Example 4 and starting from 1-(6-methoxy-2-naphthyl)-propan-1-one and 2,2-dimethyl-4(S)-methoxycarbonyl-1,3-dioxalane, 2-ethyl-2-(6-methoxy-2-naphthyl)-4(S)-methoxycarbonyl-1,3-dioxolane is prepared.

This is brominated in accordance with the procedure described in Example 5, and the brominated product rearranged and hydrolysed (in accordance with the procedure of Example 6) to give 2-(5-bromo-6-methoxy-2-naphthyl)-propionic acid with a positive value of the parameter $[\alpha]_D^{20}$.

We claim:
1. Compounds of formula

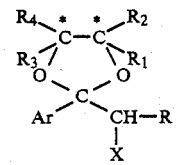

in which
Ar represents a naphthyl, unsubstituted or substituted by one or two substituents selected from the group consisting of bromine atom, methoxy, hydroxy and O-M$^+$ group wherein M$^+$ is the cation of an alkaline metal;
R represents a C$_1$–C$_4$ alkyl;
X represents a hydrogen atom;
R$_1$, R$_2$, R$_3$ and R$_4$ independently represent a hydrogen atom, a C$_1$–C$_{10}$ alkyl unsubstituted or substituted with from 1 to 4 substituents chosen from halogen atoms, C$_1$–C$_4$ alkoxy, hydroxyl, formyl, or benzyloxy groups; a phenyl unsubstituted or substituted with from 1 or 3 halogen atoms, C$_1$–C$_4$ alkyl or C$_1$–C$_4$ alkoxy; or one only of R$_1$, R$_2$, R$_3$ and R$_4$ represents a carboxyl or an alkylester of an optically active or inactive alcohol, an amide or an alkaline salt; or R$_1$+R$_3$ or R$_2$+R$_4$ together constitute a tri or tetramethylene chain unsubstituted or alkyl-substituted;
on condition that at least one of the carbon atoms indicated by an asterick is a center of asymmetry.
2. A compound as claimed in claim 1 of formula

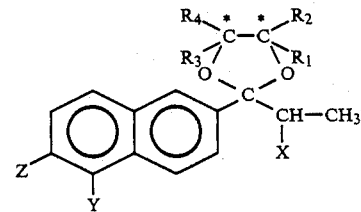

in which X, R$_1$, R$_2$, R$_3$ and R$_4$ are as defined in claim 1, Y represents a hydrogen or bromine atom, and Z represents a methoxy, hydroxyl or O$^-$M$^+$ group where M$^+$ is the cation of an alkaline metal.

* * * * *